(12) United States Patent
Liu

(10) Patent No.: US 9,055,770 B2
(45) Date of Patent: *Jun. 16, 2015

(54) MOUTHPIECE DEVICE OF ELECTRONIC CIGARETTE

(75) Inventor: Qiuming Liu, Guangdong (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 388 days.

This patent is subject to a terminal disclaimer.

(21) Appl. No.: 13/392,094

(22) PCT Filed: Dec. 23, 2011

(86) PCT No.: PCT/CN2011/084587
§ 371 (c)(1),
(2), (4) Date: Feb. 24, 2012

(87) PCT Pub. No.: WO2013/091252
PCT Pub. Date: Jun. 27, 2013

(65) Prior Publication Data
US 2013/0160764 A1    Jun. 27, 2013

(51) Int. Cl.
*A61M 15/06* (2006.01)
*A24F 47/00* (2006.01)

(52) U.S. Cl.
CPC .............. *A24F 47/008* (2013.01); *A61M 15/06* (2013.01)

(58) Field of Classification Search
USPC ...................... 128/202.21; 131/194, 270, 273
See application file for complete search history.

(56) References Cited

U.S. PATENT DOCUMENTS

| 4,917,119 | A * | 4/1990 | Potter et al. ................... 131/273 |
| 8,091,558 | B2 * | 1/2012 | Martzel ........................ 131/273 |
| 2010/0200008 | A1 * | 8/2010 | Taieb ............................ 131/360 |
| 2011/0011396 | A1 * | 1/2011 | Fang ........................ 128/202.21 |
| 2011/0036346 | A1 * | 2/2011 | Cohen et al. ............. 128/200.14 |
| 2011/0094523 | A1 * | 4/2011 | Thorens et al. ................ 131/194 |
| 2011/0126848 | A1 * | 6/2011 | Zuber et al. ................... 131/329 |

FOREIGN PATENT DOCUMENTS

GB     2190000    * 11/1987 ............ A61M 16/16

OTHER PUBLICATIONS

Rimpex Rubber. "Horizontal Vertical Compression Type Liquid Silicone Rubber Injection Molding Machine DCZ Series". Saved Mar. 17, 2009. Accessed Apr. 1, 2014. https://web.archive.org/web/20090317084958/http://www.rubberimpex.com/RubberMachinery/GDRM02Catalogue.htm.*

* cited by examiner

*Primary Examiner* — Justine Yu
*Assistant Examiner* — Kathrynn Reilly
(74) *Attorney, Agent, or Firm* — Cheng-Ju Chiang

(57) ABSTRACT

The present invention relates to a mouthpiece device of an electronic cigarette, including an atomizing device for vaporizing tobacco liquid into aerosol and a liquid reservoir for storing tobacco liquid in an inhaling shell. The atomizing device includes an atomizing cup with an atomizing chamber, and an atomizer held in the atomizing chamber. The atomizing cup is molded by an integrated process. The mouthpiece device further includes a cap at an end of the liquid reservoir, and an aerosol passage therein: The cap defines a stepped slot for filtering tobacco particles in aerosol. The stepped slot is communicated with the aerosol passage. The present invention mainly solves such problems of the existing mouthpiece device as complicated manufacturing, high cost, bad heat insulation, and failing to filter tobacco particles; and obtains a mouthpiece device with simple manufacturing, lower cost, good heat insulation and better effectiveness of filtering tobacco particles.

14 Claims, 6 Drawing Sheets

MOUTHPIECE DEVICE OF ELECTRONIC CIGARETTE

BACKGROUND OF THE INVENTION

The present invention relates to an electronic cigarette, especially to a mouthpiece device of the electronic cigarette.

Referring to FIG. 1, mouthpiece device of the existing electronic cigarette comprises an inhaling shell 1', atomizing device 2', liquid-guiding tube 3' for guiding tobacco liquid flowing therethrough, stopper 4', and cap 5'.

The shell 1' comprises a reservoir 11' for storing tobacco liquid therein and an aerosol passage 12' for allowing aerosol to pass therethrough. The atomizing device 2' comprises an atomizer 21' and an atomizing cup assembly 22' for holding the atomizer 21'. The atomizing cup assembly 22' is composed of a support seat 221', a ceramic seat 222' and a foam-nickel unit 223'. The liquid-guiding tube 3' has one end thereof connected with the reservoir 11' through a metal frame 6' so as to guide the tobacco liquid from the reservoir 11' to the atomizing cup assembly 22'. The stopper 4' is inserted in the reservoir 11' at one end facing the atomizing device 2', and the cap 5' is used for sealing the other end of the reservoir 11'.

However, the existing mouthpiece device of the electronic cigarette has such disadvantages that: it is very complicated to manufacture and assemble the atomizing cup assembly 22', the manufacturing cost is high; the ceramic seat 222' and foam-nickel unit 223' directly contact with an inner wall of the shell 1' which results unsatisfactory heat insulation, therefore, the temperature at outer wall of the shell 1' is relatively high even to be felt burning hand, and the electronic cigarette cannot be used; the metal frame 6' does not facilitate liquid-guiding, but raises the manufacturing cost; moreover, the cap 5' is set at an inhaling end of the shell 1', the aerosol passage 12' directly extends to outside of the shell 1', therefore, tobacco particles will flow together with aerosol from the aerosol passage 12' to outside of the shell 1', and thus fail to be filtered.

BRIEF SUMMARY OF THE INVENTION

A main object of the present invention is to provide a mouthpiece device of an electronic cigarette, which facilitates manufacturing, reduces cost, and has good heat insulation.

Another object of the present invention is to provide a mouthpiece device of an electronic cigarette, which perfectly filter tobacco particles.

To obtain the above object, a mouthpiece device of an electronic cigarette comprises an inhaling shell, an atomizing device within the inhaling shell for vaporizing tobacco liquid into aerosol, and a liquid reservoir inside the inhaling shell for storing tobacco liquid therein. The atomizing device comprises an atomizing cup with an atomizing chamber therein, and an atomizer held in the atomizing chamber. The atomizing cup is an integrated cup body made in one mould.

Further, the atomizing cup comprises a mounting seat disposed in the atomizing chamber for holding the atomizer, and defines wire-through holes for passing electric wire therethrough. The wire-through holes are defined in the atomizing cup and communicated with the atomizing chamber.

Further, the atomizing cup is shaped as a cylinder, has a figuration and dimension adapted for an inner wall of the inhaling shell, and defines a through heat-dissipation hole in center thereof.

Further, the atomizing cup is made from silica gel.

Further, the mouthpiece device comprises a liquid-guiding tube and a stopper which is disposed at one end of the liquid reservoir. One end of the liquid-guiding tube is inserted through the stopper and extends to the liquid reservoir. The stopper defines a tube hole, and the liquid-guiding tube is engaged in the tube hole by an interference fit, sealing material circularly inserted therebetween.

Further, the mouthpiece device comprises a cap for sealing the other end of the liquid reservoir, and an aerosol passage defined in the mouthpiece device. The cap defines an air slot for depositing tobacco particles on surface thereof, and a suction hole for air communicating in and out of the inhaling shell. The air slot is communicated with the aerosol passage, and the suction hole is also communicated with the aerosol passage.

Further, the air slot is stepped, and the stepped air slot is communicated with the suction hole. The aerosol passage is communicated with the suction hole through the stepped air slot. Otherwise, the air slot runs through the cap from a top end to a bottom end thereof, is positioned in sidewall of the cap, and is depressed towards a center line of the cap.

Further, the cap is made from silica gel and is an integrated structure by an integrated molding process, and has a configuration and dimension adapted for an inner chamber of the inhaling shell.

Further, a filtering layer is set on an inner wall of the aerosol passage according to a cross section of the aerosol passage.

Further, the filtering layer is a filtering plate with at least one filtering hole defined therein. The filtering plate is set on the inner wall of the aerosol passage and perpendicularly to a central line of the aerosol passage, and is integrated with the inner wall of the aerosol passage.

The advantages of the present invention are that: the mouthpiece device has an integrated atomizing cup, which facilitates manufacturing and reduces cost; and the atomizing cup has good heat insulation performance; furthermore, the mouthpiece device has a filtering plate and the cap with filtering function, which render the mouthpiece device to preferably filter tobacco liquid.

A further detailed description to the present invention follows with reference to the accompanying drawings.

DETAILED DESCRIPTION OF THE INVENTION

Figure 1:
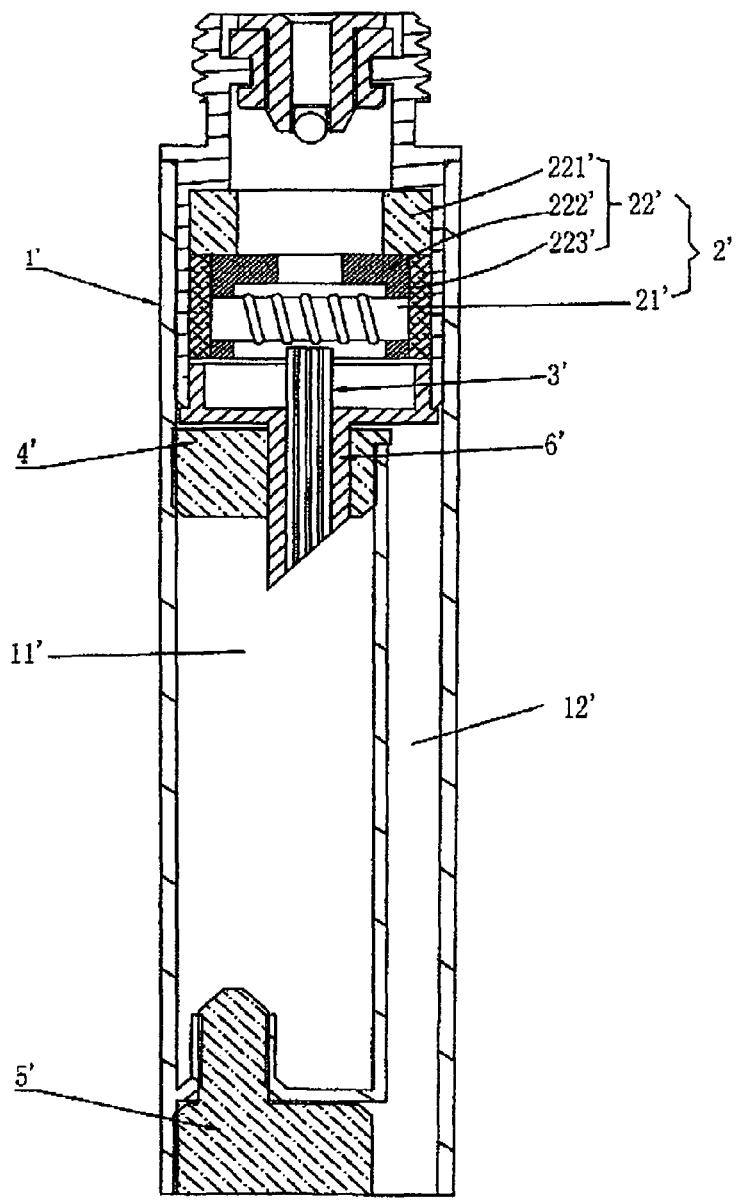
FIG. 1 is a schematic view of a mouthpiece device of an electronic cigarette of prior art.
Figure 2:
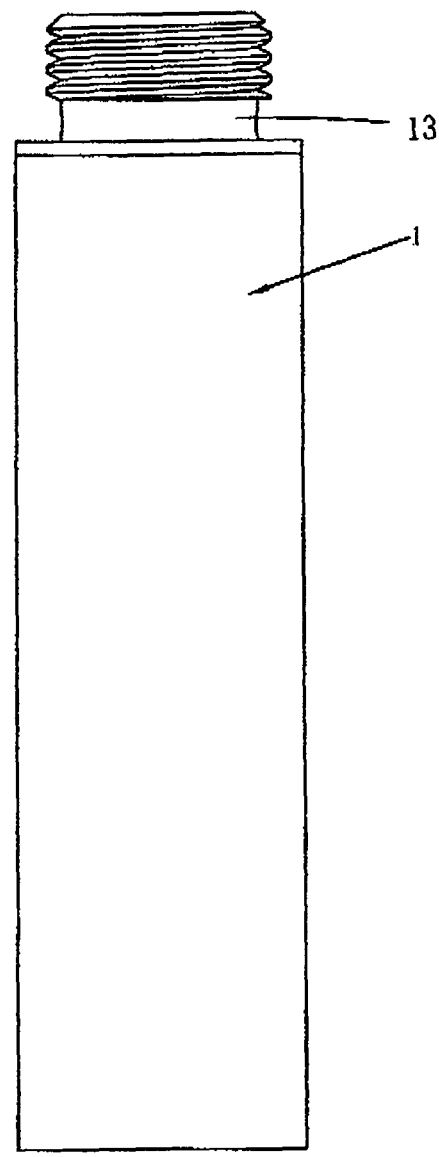
FIG. 2 is a front view of a mouthpiece device of an electronic cigarette of the present invention.
Figure 3:
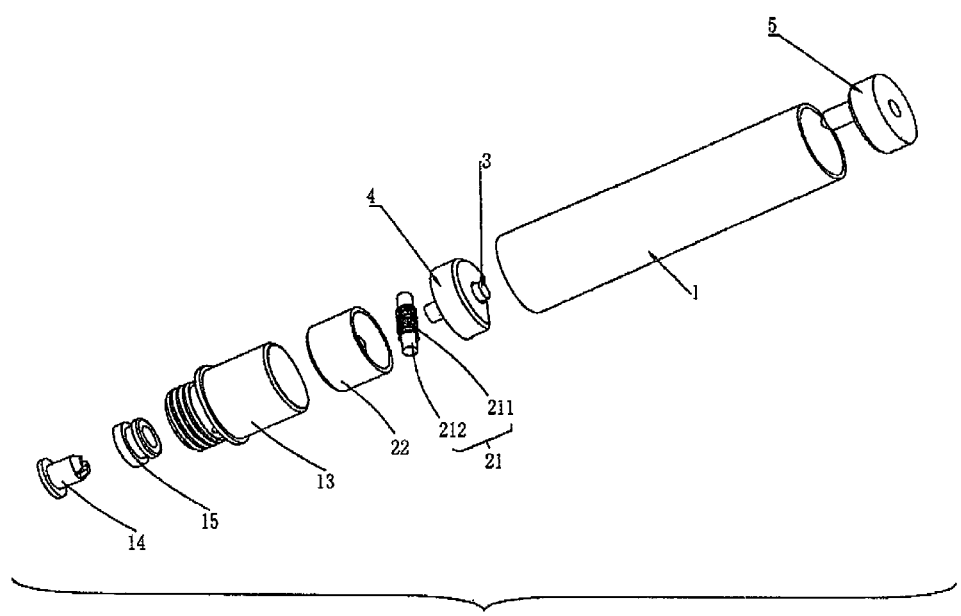
FIG. 3 is an exploded view of the mouthpiece device of the present invention.
Figure 4:
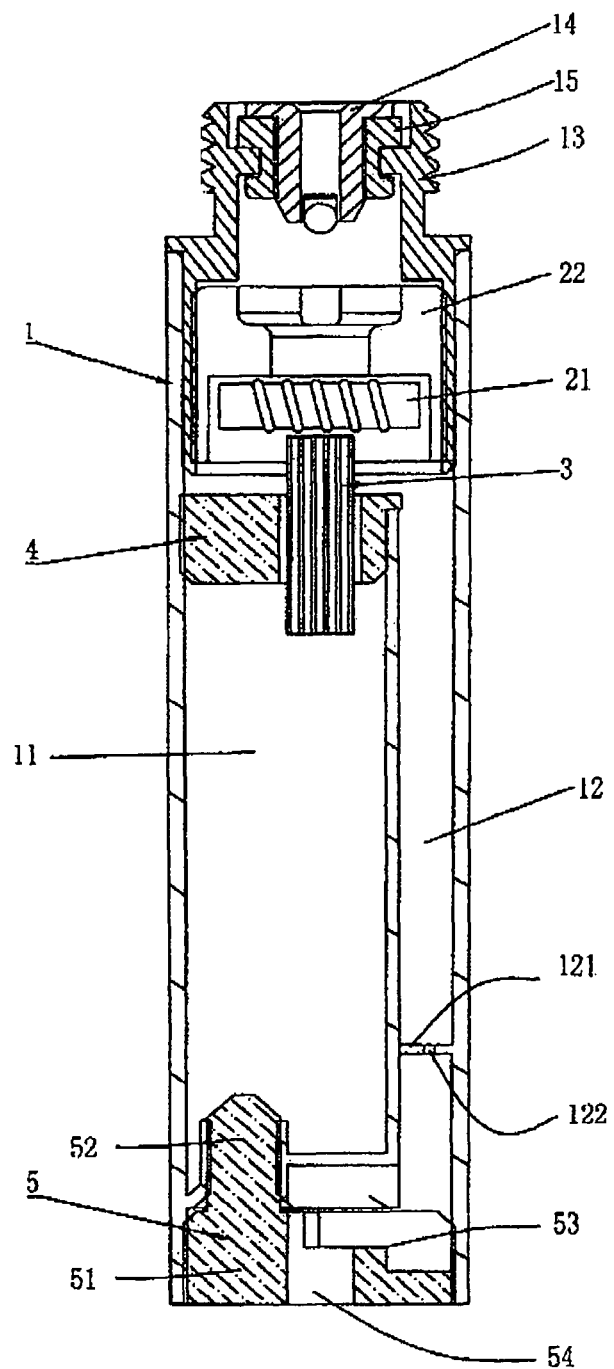
FIG. 4 is a cross-section view of the mouthpiece device of the present invention.
Figure 5:
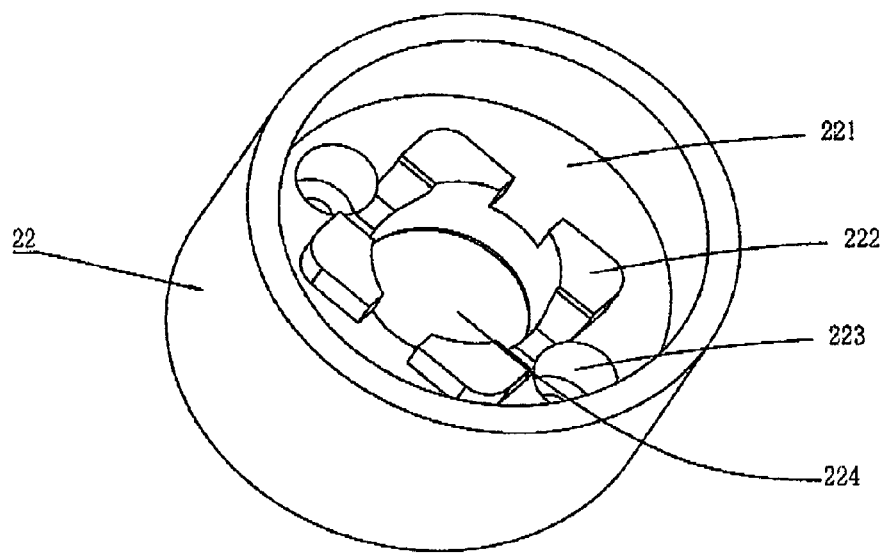
FIG. 5 is a perspective view of an atomizing cup of the mouthpiece device of the present invention.
Figure 6:
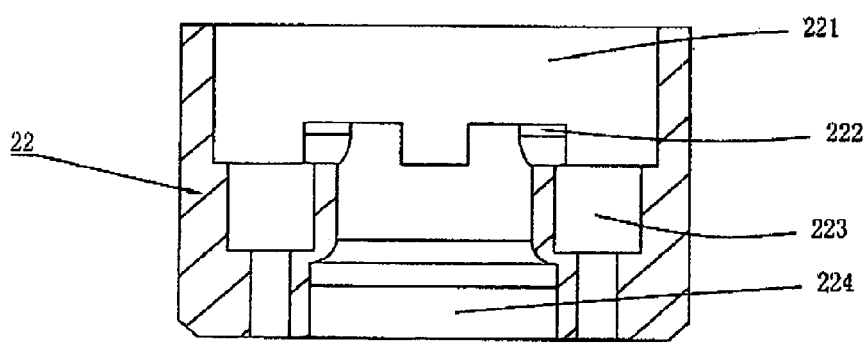
FIG. 6 is a cross-section view of the atomizing cup of the mouthpiece device of the present invention.

Referring to FIGS. 2-8, the present invention provides a mouthpiece device of an electronic cigarette and a filtering device thereof. The mouthpiece device comprises an inhaling shell 1 with two open ends, an atomizing device 2, a liquid-guiding tube 3, a stopper 4, and the filtering device which has a cap 5 or cap 5". One of the open end of the inhaling shell 1 is used as a connecting end for connection with a power supply part of the electronic cigarette, and the other open end is used as an inhaling end for user's suction and is covered with the cap 5 or 5".

The inhaling shell 1 comprises a liquid reservoir 11, an aerosol passage 12 alongside the liquid reservoir 11, a connection element 13, an electrode element 14, and an insulating ring 15. The liquid reservoir 11 and the aerosol passage 12 are longitudinally set in the shell 1. The first ends as inner ends of both the liquid reservoir 11 and the aerosol passage 12 are open side by side and facing the atomizing device 2 within the inhaling shell 1, and the second ends of both the liquid reservoir 11 and the aerosol passage 12 are facing the inhaling end of the inhaling shell 1. In this embodiment, the liquid reservoir 11 is integrated in the shell 1. The liquid reservoir 11 is used to store tobacco liquid, and has the inner end thereof set with the stopper 4, and has the second end set with the cap 5. Thus the stopper 4 and cap 5 together seal tobacco liquid in the reservoir 11. The aerosol passage 12 is used for aerosol to flow therethrough to an inhaling end of the shell 1 after tobacco liquid is vaporized to generate aerosol by the atomizer 2. A filtering layer is set on inner wall of the aerosol passage 12. The filtering layer is set on the inner wall of the aerosol passage 12, and is adapted for a cross section of the inner wall. In this embodiment, the filtering layer is a filtering plate 121 integrated with the inner wall of the aerosol passage 12. The filtering plate 121 is set perpendicularly to a central line of the aerosol passage 12, and defines at least one filtering hole 122 therethrough. The connection element 13 is disposed at the connecting end of the shell 1. One end of the connection element 13 with external threads thereon is threadedly connected with the power supply part (not shown) of the electronic cigarette, and the other end thereof is inserted in the shell 1. The connection element 13 defines a cylindrical chamber inside for receiving the atomizing device 2, and defines a mounting groove inside for holding the electrode element 14 therein. The connecting part 13 itself as an electrode of the atomizing device 2 is electrically connected with electrode of the power supply part. The electrode element 14 is fitted in the mounting groove of the connection element 13 in virtue of inserting the insulating ring 15 therebetween. The electrode element 14 has an end contacted with a corresponding electrode of the power supply part so as to energize an electric circuit.

The atomizing device 2 comprises an atomizer 21 and an atomizing cup 22. The atomizer 21 comprises an electric heat wire 211 and an electric heat rod 212. The electric heat wire 211 winds around the heat rod 212, and is mounted in the atomizing cup 22 by means of the heat rod 212. The atomizing cup 22 is an integrated and inseparable cup body made in one mould, and comprises an atomizing chamber 221, a mounting seat 222 with a fixing groove therein, wire-through holes 223, and a through heat-dissipation hole 224 in center of the atomizing cup 22.

The mounting seat 222 with the fixing groove therein integrally and inseparably extends from a bottom of the atomizing chamber 221 up to a certain height, which is used for holding the atomizer 21. The electric heat rod 212 is fixed in the fixing groove of the mounting seat 222 in a diameter direction of the atomizing cup 22 and facing one end of the liquid-guiding tube 3. The wire-through holes 223 are used to pass electric wires therethrough, and are disposed in the atomizing cup 22 and communicated to the atomizing chamber 221. There are two wire-through holes in this embodiment. An electric wire connecting one end of the heat rod 212 passes one wire-through hole 223 to electrically connect with the connection element 13, another electric wire connecting the other end of the heat rod 212 passes the other wire-through hole 223 to electrically connect with electrode element 14. The heat-dissipation hole 224 is used to transfer heat from the atomizer to the power supply part. In this embodiment, the atomizing cup 22 is disposed in the shell 1 in virtue of the connection element 13, the atomizing cup 22 is held in the connection element 13, and the dimension and figuration thereof are designed corresponding to the cylindrical chamber of the connection element 13. The material for the atomizing cup 22 has good heat resistance, such as silica gel, which renders the atomizing cup 22 with good heat insulation. The atomizing cup 22 is shaped as a cylinder, and has a diameter larger than that of the cylindrical chamber of connection element 13 so as to be tightly fitted in the connection element 13. The atomizing cup 22 of this embodiment not only facilitates manufacturing of the mouthpiece device, but also reduces the cost. Furthermore, since the atomizing cup 22 is made from silica gel with good heat resistance, which provides a good heat insulation, the temperature at outer wall of the mouthpiece device keeps relatively low, and will not burn hand or mouth.

The liquid-guiding tube 3 is used to guide tobacco liquid from reservoir 11 to atomizing chamber 221 for atomization. The liquid-guiding tube 3 has a first end thereof directly passing through the stopper 4 and extending in the reservoir 11 and a second end extending into the atomizing device 2. The liquid-guiding tube 3 is engaged with the stopper 4 by interference fit, and is made from glass fiber.

The stopper 4 is used for sealing the liquid reservoir 11, and defines a tube hole therein. The liquid-guiding tube 3 is engaged in the hole by interference fit, and sealing material is circularly inserted between contacts of both.

Figure 7:
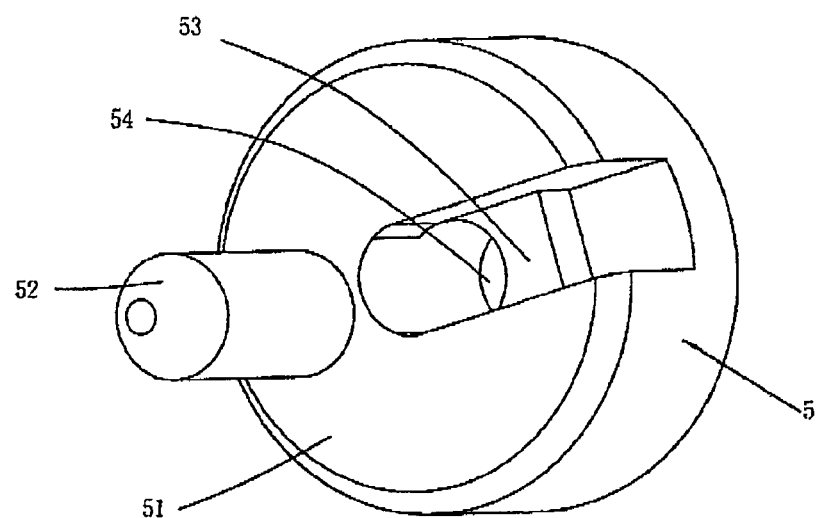
FIG. 7 is a perspective view of a cap of the mouthpiece device in accordance with a first embodiment of the present invention.

Referring to FIG. 7, in the first embodiment, the cap 5 comprises a main body 51, a plug 52 extending from bottom of the main body, an air slot 53, and a suction hole 54. The cap 5 seals the reservoir 11 in such way that the plug 52 is inserted in the reservoir 11 from the inhaling end of the shell 1. The air slot 53 is stepped and shaped as letter Z. The air slot 53 is positioned along the same diameter as the plug 52, and is communicated with the aerosol passage 12. The suction hole 54 is used for air communicating between inside and outside of the shell 1. The suction hole 54 is communicated with the air slot 53, and the aerosol passage 12 communicates with the suction hole 54 through the air slot 53. The dimension and figuration of the cap 5 are designed according to inner diameter of the inhaling end of the shell 1. In this embodiment, the cap 5 is shaped as a cylinder, and is made from silica gel. The diameter of the cap 5 is larger than inner diameter of the shell 1 so that the cap 5 is tightly fitted in the shell 1 by means of a circumferential sidewall of the cap 5 being tightly fitted in a circumferential inner wall of the inhaling shell 1.

Figure 8:
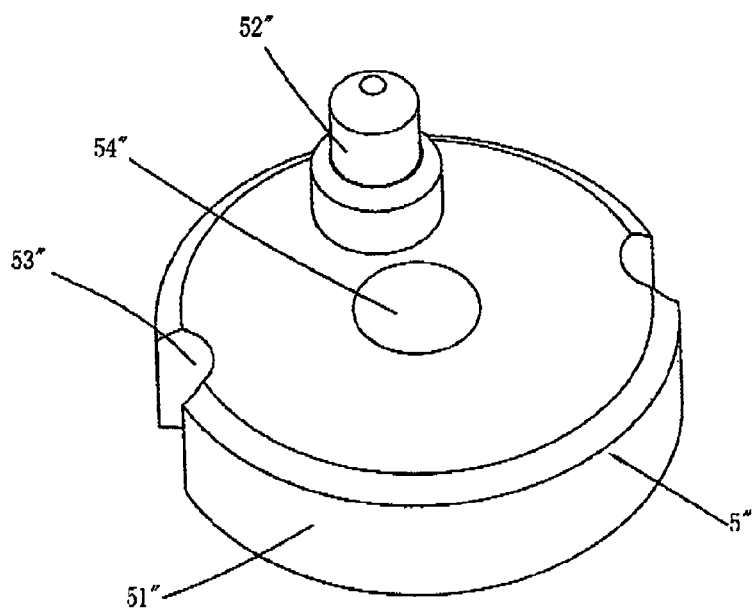
FIG. 8 a perspective view of the cap of the mouthpiece device in accordance with a second embodiment of the present invention.

Referring to FIG. 8, in the second embodiment, the cap 5" comprises a main body 51", a plug 52" extending from bottom of the main body, air slots 53", and suction hole 54". The cap 5" is mainly similar to the cap 5 in the first embodiment, but it is different that the air slot 53" runs through the cap 5" from a top end to a bottom end of the main body, is positioned in the sidewall of the cap 5", and is a concave parallel to a center line of the cap. The air slots directly communicate with the aerosol passage 12, and has a cross-section shaped as arc, letter U or V.

The filtering layer and the cap 5 or cap 5" constitute the filter device. The tobacco liquid is guided from reservoir 11 to atomizer 21 which vaporizes the liquid drops into aerosol mixed with tobacco particles. The aerosol flows into the aerosol passage 12, and are firstly filtered by the filtering plate 121. The aerosol passes through the filtering hole 122 of the filtering plate 121 to next part of the aerosol passage, while aerosol flows to the filtering plate 121 and thus confronts resistance thereof, tobacco particles mixed in aerosol deposit on the filtering plate 121, so that tobacco particles are filtered from aerosol. Then, aerosol keeps to flow along the passage 12, and is secondly filtered by the cap 5. Aerosol flows from the passage 12, then passes from the air slot 53 and through the suction hole 54, and finally flows to outside of shell 1. Or, aerosol flows from the passage 12 and through the air slot 53", then directly to outside of shell 1. Since air slot 53 or 53" provides resistance to the movement of the aerosol, other tobacco particles are deposited in the air slot 53 or 53' for the purpose of being filtered and so as to prevent more tobacco particles flowing to outside of the shell 1 or being inhaled by human body.

In the view of disclosure to the embodiments of the present invention, it will be apparent to one skilled in the art that modifications and/or substitutes may be made without departing from the scope and spirit of the invention.

What is claimed is:

1. A mouthpiece device of an electronic cigarette comprising an inhaling shell, an atomizing device within the inhaling shell for vaporizing tobacco liquid into aerosol, a liquid-guiding tube, a stopper, a cap, and a connection element;
   wherein both ends of the inhaling shell are open, one of the open end of the inhaling shell is used as a connecting end for connection with a power supply part of the electronic cigarette, the other open end is used as an inhaling end for user's suction and is covered with the cap;
   the inhaling shell longitudinally forms a liquid reservoir and an aerosol passage side by side within the inhaling shell, first ends as inner ends of both the liquid reservoir and the aerosol passage are open and facing the atomizing device, and second ends of both the liquid reservoir and the aerosol passage are facing the inhaling end of the inhaling shell;
   tobacco liquid is sealed in the liquid reservoir;
   the stopper seals the inner end of the reservoir;
   the liquid-guiding tube is inserted through the stopper and guides tobacco liquid from the reservoir into the atomizing device;
   the cap defines a suction hole therethrough for passing aerosol from the second end of the aerosol passage to outside of the inhaling end for user's suction, and the cap is inserted at the inhaling end of the inhaling shell and removably seals the second end of the reservoir;
   the connection element as an electrode of the atomizing device is inserted in the connecting end of the inhaling shell and defines a cylindrical chamber therein for receiving the atomizing device;
   the atomizing device comprising an atomizing cup and an atomizer;
   the atomizing cup is an integrated and inseparable cup body made from silica gel in one mould, has a cylindrical shape in a diameter larger than that of the cylindrical chamber of connection element, and is tightly fitted in the connection element; the atomizing cup defines an atomizing chamber therein facing and communicating with the inner ends of both the liquid reservoir and the aerosol passage, and comprises a mounting seat integrally and inseparably extending away from a bottom of the atomizing chamber for a preset distance to engage with the atomizer in the atomizing chamber;
   wherein said cap defines an air slot for depositing tobacco particles on surface thereof, the air slot is communicated with the aerosol passage, and the suction hole is also communicated with the aerosol passage and is used for air communicating between inside and outside of the inhaling shell,
   wherein said air slot is stepped and shaped as letter Z, and the stepped air slot is communicated with the suction hole, the aerosol passage is communicated with the suction hole through the stepped air slot.

2. The mouthpiece device according to claim 1, wherein the atomizing cup further longitudinally defines wire-through holes for passing electric wire through the bottom of the atomizing chamber; the wire-through holes are communicated with said atomizing chamber.

3. The mouthpiece device according to claim 1, wherein the atomizing cup has a figuration and dimension adapted for an inner wall of the inhaling shell, and defines a through heat-dissipation hole in center of the bottom of the atomizing chamber.

4. The mouthpiece device according to claim 1, wherein a first end of the liquid-guiding tube is inserted through the stopper and extends to the liquid reservoir, and a second end of the liquid-guiding tube extends to the atomizing device; the stopper defines a tube hole therethrough, an outer surface of the liquid-guiding tube is fitted on an inner surface of the stopper in the tube hole with sealing material circularly inserted therebetween; and the liquid-guiding tube is made from glass fiber.

5. The mouthpiece device according to claim 1.

6. The mouthpiece device according to claim 1, wherein a filtering plate is set on an inner wall of the aerosol passage according to a cross section of the aerosol passage.

7. The mouthpiece device according to claim 6, wherein the filtering plate at least defines one filtering hole therein; the filtering plate is set on the inner wall of the aerosol passage and perpendicularly to a central line of the aerosol passage, and is integrated with the inner wall of the aerosol passage.

8. The mouthpiece device according to claim 5, wherein the air slot runs through the cap from a top end to a bottom end thereof, is positioned in the sidewall of the cap, and is a concave parallel to a center line of the cap; the air slots directly communicate with the aerosol passage, and has a cross-section shaped as arc, letter U or V.

9. The mouthpiece device according to claim 4, wherein the atomizer comprises the electric heat wire and an electric heat rod, the electric heat wire winds around the heat rod; the mounting seat defines a fixing groove on its top and holds the atomizer in the fixing groove to keep the heat rod in a diameter direction of the atomizing cup and facing the second end of the liquid-guiding tube.

10. The mouthpiece device according to claim 1, further comprising an electrode element and an insulating ring, wherein the electrode element is fitted in the connection element in virtue of inserting the insulating ring therebetween.

11. The mouthpiece device according to claim 1, wherein the liquid reservoir is integrated in the inhaling shell.

12. The mouthpiece device according to claim 1, wherein one end of the connection element forms external threads therearound and is threadedly connected with the power supply part of the electronic cigarette, and the other end thereof is inserted in the inhaling shell.

13. The mouthpiece device according to claim 1.

14. The mouthpiece device according to claim 13, wherein the air slot is positioned along the same diameter as the plug.

\* \* \* \* \*